(12) United States Patent
Luecker et al.

(10) Patent No.: US 8,192,242 B2
(45) Date of Patent: Jun. 5, 2012

(54) FORCE SENSING OAR

(76) Inventors: Michael C. Luecker, Corvallis, OR (US); Michael H. Linse, Corvallis, OR (US)

( * ) Notice: Subject to any disclaimer, the term of this patent is extended or adjusted under 35 U.S.C. 154(b) by 250 days.

(21) Appl. No.: 12/645,386

(22) Filed: Dec. 22, 2009

(65) Prior Publication Data
US 2010/0167606 A1  Jul. 1, 2010

Related U.S. Application Data

(60) Provisional application No. 61/203,809, filed on Dec. 29, 2008.

(51) Int. Cl.
*B63H 16/04* (2006.01)
*B63H 16/10* (2006.01)

(52) U.S. Cl. ........................................... 440/101

(58) Field of Classification Search .......... 440/101–110; 701/21; 482/9, 148
See application file for complete search history.

(56) References Cited

U.S. PATENT DOCUMENTS

| | | | |
|---|---|---|---|
| 4,735,410 A * | 4/1988 | Nobuta | 482/9 |
| 4,984,986 A | 1/1991 | Vohnout | |
| 5,099,689 A | 3/1992 | McGinn | |
| 6,980,118 B2 | 12/2005 | Buvac | |
| 7,114,398 B2 | 10/2006 | Haines | |
| 7,207,853 B2 | 4/2007 | Spencert et al. | |
| 7,828,706 B2 * | 11/2010 | Medina | 482/148 |
| 2005/0085348 A1 | 4/2005 | Kiefer et al. | |
| 2005/0215870 A1 | 9/2005 | Rademaker | |

OTHER PUBLICATIONS

Baudouin et al., "Investigation of Biomechanical Factors Affecting Rowing Performance," *Journal of Biomechanics*, vol. 37, 969-976 (2004).
Bompa et al., "Force Analysis of the Rowing Stroke Employing Two Differing Oar Grips," *Canadian Journal of Applied Sport Sequences*, vol. 10 (2), 64-67 (1985).
Davis et al., "Oar Forces from Unobtrusive Optical Fibre Sensors," 2007, 6 pp., published in Fuss et al. (eds.), *The Impact of Technology on Sport II* (2007).
Weba Sport, "Why Become a Professional?", http://www.eba.sport.com/weba/rower_expert_light.html, Apr. 26, 2004.

* cited by examiner

*Primary Examiner* — Daniel Venne
(74) *Attorney, Agent, or Firm* — Stoel Rives LLP; Robert R. Teel

(57) ABSTRACT

A system for determining the magnitude of force applied to an oar by a rower as the oar is pulled through water includes a deflection sensor and a temperature sensor mounted on an oar shaft to determine deflection and temperature of a portion of the oar shaft during rowing. A processor connected to the deflection sensor and the temperature sensor receives signals indicative of deflection and temperature of the oar shaft and derives a force applied to an oar blade based on the deflection and temperature signals.

18 Claims, 5 Drawing Sheets

FORCE SENSING OAR

RELATED APPLICATIONS

This application claims priority under 35 U.S.C. §119(e) to U.S. Patent Application No. 61/203,809 titled "Precision Rowing Oar—P.R.O." and filed on Dec. 28, 2008, which is fully incorporated by reference herein.

TECHNICAL FIELD

The present disclosure relates to a rowing oar, and in particular, a rowing oar for determining a magnitude of force acting on the oar blade when a rower moves the oar blade through water.

BACKGROUND

The present inventors have recognized that common practices for coaching rowing teams involves several aspects that coaches use to assess each individual rower's performance to determine which combination of rowers will likely row a boat the fastest. One aspect is knowing which individuals are rowing with the most force so coaches have an idea of who is moving the boat through the water most powerfully. Another aspect is tracking each individual's force output over time to pair rowers with complementary force-outputs and rowing styles as teammates in a boat. Yet another aspect is to improve competitive results using information about individual performance.

The present inventors have also recognized that inexperienced rowers commonly have several challenges to address while learning to row. For example, inexperienced rowers commonly start out rowing in a manner that feels natural and may mistakenly believe a rowing stroke is powerful when in fact the rowing form is incorrect. Incorrect rowing form results in a weaker rowing stroke. Another challenge is that when a rowing coach instructs inexperienced rowers to correct their form, the inexperienced rowers may be unsure how to make the stroke more powerful using the new and unfamiliar rowing form. As a result, inexperienced rowers may be reluctant to change their form and may fall back into using poor form. The present inventors have also recognized that providing stroke force magnitude to rowers may help them recognize how form changes increase the power of their stroke and that inexperienced rowers may benefit from individualized rowing information.

The present inventors have also recognized that several common performance assessment tools rowing coaches currently use do not provide accurate on-the-water information regarding a rower's stroke. One such common assessment tool is to measure rowing power performance primarily using an ergometer. Coaches commonly use ergometers to compare individual rowing data for a set of rowers to select a combination of rowers for a boat. Each individual's quantitative rowing data is also collected from successive ergometer workout sessions to track each individual's rowing performance. The present inventors have recognized that the quantitative data collected from ergometers is not necessarily indicative of rowing performance on the water. The present inventors have also recognized that, for various reasons, rowers often perform differently in a boat on the water than they do on the ergometer. For example, the present inventors have recognized that the ideal body type for rowing on the water is somewhat different from the ideal body type for ergometer rowing. Additionally, the present inventors have recognized that rowing performance on water is dependent on oar handling, which is not required on an ergometer. Furthermore, the present inventors have recognized that an ergometer does not require a rower to maintain the balance of a boat using his or her body motion. The present inventors have further recognized that rowing on land using an ergometer does not equate to rowing on water, that the quantitative measurements taken with an ergometer cannot reliably indicate rowing performance on the water, and that an ergometer therefore provides a rower or coach only a limited indication of performance on the water. The present inventors have also recognized that ergometer performance alone should not be the basis for competitive boat line-ups.

Another performance assessment tool coaches currently rely on are seat races. Seat races are used to assist coaches' decisions regarding which rowers to place in a top boat during competitive races against other teams. During a seat race, two boats typically race against each other twice. At the end of the first race one rower from each boat is replaced by a new rower. The two boats race again and the relative performance of the boats during the two races is used to compare the abilities of the two rowers who were replaced and of the two new rowers. The present inventors have recognized that observational data from seat races depends on the performance of all the rowers participating in the seat race, and therefore a seat race cannot truly isolate individual performance because the coach simply cannot easily tell who the powerful rowers are. The present inventors have also recognized that seat races can be particularly inconclusive and inefficient if coaches have multiple rowers to observe during the race. Furthermore, the present inventors have recognized that a rowing team with only one boat and multiple rowers trying to get a seat in that boat must address additional logistical and timing problems associated with seat races in a single boat. For example, a team with only one boat must time the first race and then wait until the original rowers are completely rested before replacing one of the rowers and timing the second race.

Other tools rowers and coaches use to collect quantitative data of rowing performance are force-sensing systems on boat components. These force-sensing systems have used strain gages to measure the force on various components in a boat. An example of measuring the force applied to an oarlock is in U.S. Pat. No. 7,114,398 of Haines that describes a load cell with strain gages adapted for use in an oarlock. Another example is in U.S. Pat. No. 7,207,853 of Spencert et al. that describes an oarlock modified to incorporate a strain gage used for measuring a strain in a bearing of the oarlock caused by a force of the oar upon the oarlock during a stroke. Strain gages have also been incorporated in the foot stretchers of a boat to measure the deflection of the foot stretcher. Another example of a strain gage system is disclosed in U.S. Pat. No. 5,099,689 of McGinn.

The present inventors have recognized that adding current force-sensing systems to a boat typically requires bulky equipment that adds additional weight to the boat. The present inventors have recognized that additional equipment also commonly requires modifications to the oarlocks, foot stretchers, or the boat, which coaches and crews are often unwilling to make. The present inventors have also recognized that current force-sensing systems require frequent calibration to provide accurate force measurements.

For the foregoing reasons, the present inventors have recognized a need for a rowing oar equipped to determine a magnitude of force acting on the oar blade to provide individualized rowing force information to coaches and rowers.

SUMMARY OF DISCLOSURE

The present disclosure is directed to a system and method for providing performance feedback from a rowing oar, and in a preferred configuration, an oar equipped with a processor, a power supply, and deflection and temperature sensors is used to determine rowing force based on the temperature-dependant elastic properties of the oar. A system and method directed to providing coaches and rowers individualized rowing force information in a cost-effective and manageable way is disclosed.

A preferred system of an oar for determining a force of a rower's rowing stroke in water includes a handle, an oar shaft extending from the handle, an oar blade affixed to the oar shaft, a deflection sensor, a temperature sensor, a processor operatively connected to the temperature and deflection sensors, and a display device operatively connected to the processor. The deflection sensor is preferably a strain gage affixed to the oar shaft for sensing oar shaft deflection resulting from a force acting on the oar blade. The temperature sensor is preferably a thin-film temperature sensor affixed to the oar shaft proximate the deflection sensor. The processor receives deflection and temperature data and is programmed to determine a magnitude of force acting on the oar blade based on the deflection and temperature data. The deflection and temperature sensors are preferably embedded within the oar shaft under the collar but may also be affixed to the outside or the inside surfaces of the oar shaft. The display device receives information from the processing device and displays the determined force magnitude. The display device may also be used to view rowing data derived from force magnitude determinations with or without timing information.

Additional aspects and advantages will be apparent from the following detailed description of preferred embodiments, which proceeds with reference to the accompanying drawings.

DETAILED DESCRIPTION OF PREFERRED EMBODIMENTS

This disclosure describes a self-contained oar device that does not require boat modifications, vulnerable cabling, frequent calibration, or additional bulky equipment. While the following discussion references a preferred embodiment having a specific sensor placement and using a specific processor and display configuration, the invention is not limited to the particular details discussed. The invention is defined by claims in this non-provisional application.

Figure 1:
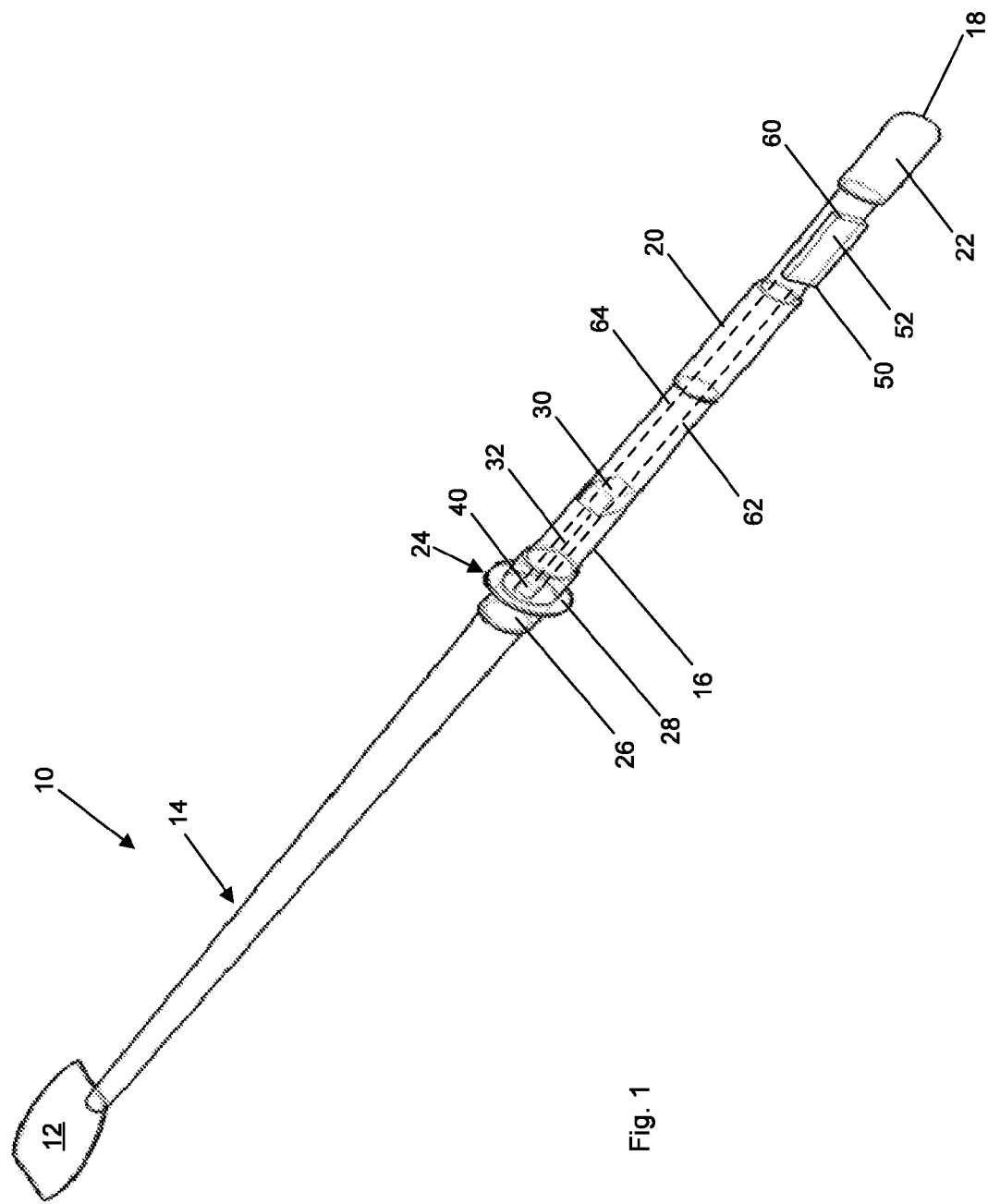
FIG. 1 is an isometric view of an oar according to a preferred embodiment.
Figure 1A:
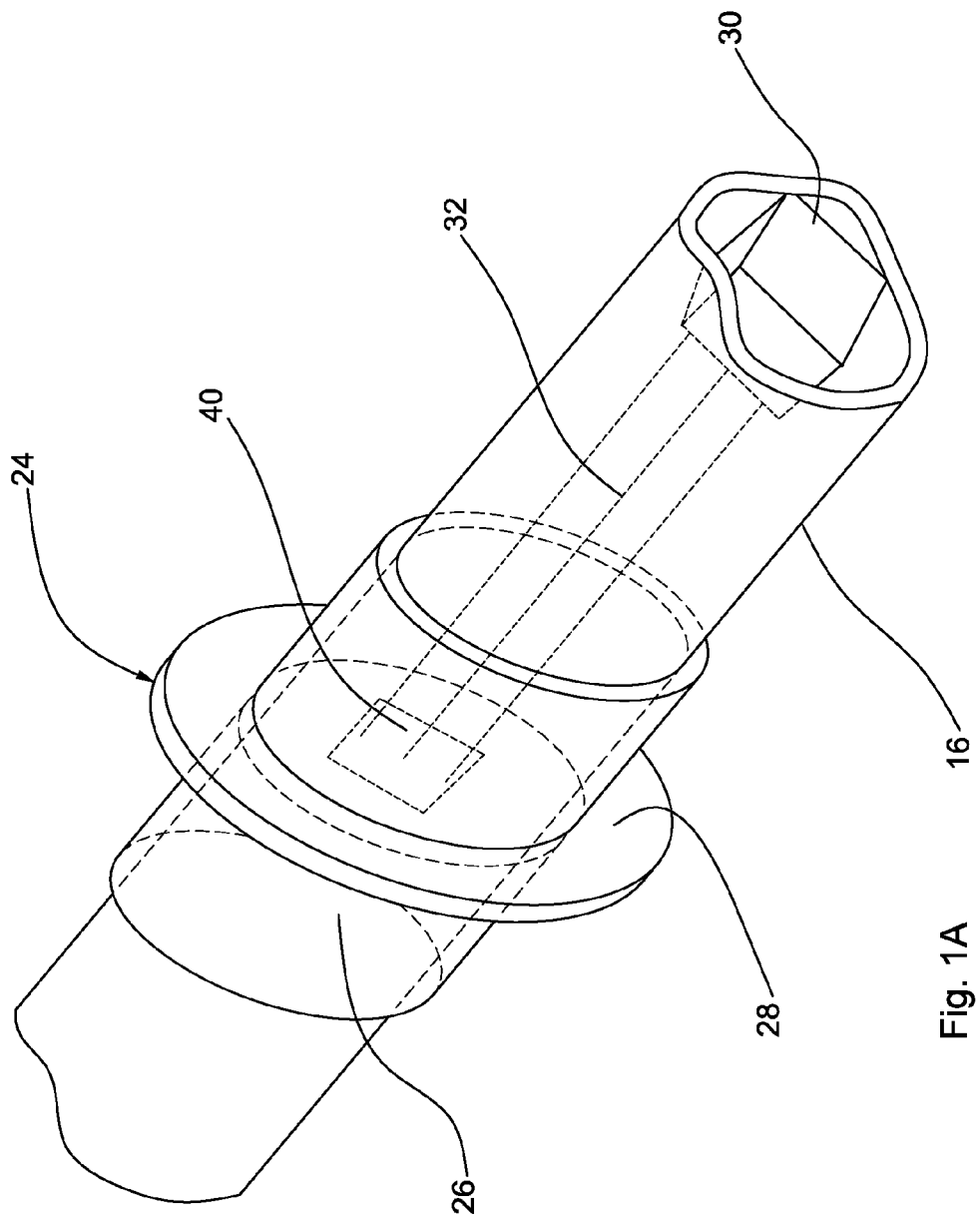
FIG. 1A is an enlarged view of a section of the oar shown in FIG. 1, showing details of a collar, a disk shaped button, and a molded sleeve.

FIG. 1 shows sweep-rowing oar 10. Alternately oar 10 may be another suitable oar such as, but not limited to, a sculling oar. Oar 10 is either a port or starboard sweep oar capable of being used by any rower in an 8+, 4+, or pair crew shells. Oar 10 is designed for use by competitive high school rowing teams, club organizations, collegiate, and Olympic organizations. With respect to FIG. 1, in a preferred embodiment oar 10 has cleaver oar blade 12 attached to the end of loom 14 of hollow oar shaft 16. Oar shaft 16 is generally tubular and is constructed from a lightweight and rigid graphite-epoxy composite. Distal from oar blade 12, handle 18 of oar shaft 16 includes inner grip 20 and outer grip 22 affixed and conforming around oar shaft 16. Inner 20 and outer 22 grips are preferably constructed of high-density moisture repelling foam that provides a reliable grip surface for a rower while simultaneously reducing the rower's possibility of hand blisters. Collar 24 (as shown in detail in FIG. 1A) affixed and conforming around oar shaft 16 is located approximately two-thirds along the length of oar shaft 16 away from the oar blade 12. The collar 24 contains a molded sleeve 26 (FIG. 1A) to assist a rower when he or she is squaring and feathering oar 10. The molded sleeve 26 is generally tube-shaped to conform to the outer surface of oar shaft 16, with the exception of wear plate (not shown) on molded sleeve 26 that is substantially flat to engage an oarlock (not shown) during the drive portion of a rowing stroke. Collar 24 also contains a disk-shaped button 28 (FIG. 1A) which forms a concentric ring shape around molded sleeve 26. The button 28 provides a pivot point that prevents oar 10 from sliding through the oarlock while a rower is rowing.

Power source 30 conveys electrical power via wires 32 running within the internal hollow space of oar shaft 16. In the preferred embodiment described, power source 30 is a rechargeable battery pack housed in the internal void space of hollow oar shaft 16. Power source 30 is rechargeable using an inductive charging system such that no metal contacts are exposed on the outside surface of oar 10. Inductive charging protects the internal electrical components from the weather. Alternatively, power source 30 is recharged using a mechanical power harvesting device such as a magnet caused to move through a metal coil when oar 10 is used. Power source 30 may also be recharged using solar cells; however, solar cells are vulnerable to weather and require electrical wiring via holes in oar 10 that could potentially cause a leak when exposed to moisture.

Sensor kit 40 is positioned at a location on oar 10 that experiences measurable compressive or tensile deflection during rowing. In a preferred arrangement sensor kit 40 includes a suitable deflection detector, such as strain gage 42 like the SGD-10/1000-LY43 manufactured by Omega Engineering of Stamford, Conn., and a suitable temperature sensor, such as thin-film temperature sensor 44 like the Thermal-Ribbon manufactured by Minco Products, Inc. of Minneapolis, Minn. A suitable temperature sensor preferably has a low thermal mass compared to the thermal mass of the portion of the oar shaft for which the temperature sensor detects the temperature. A temperature sensor with a relatively large thermal mass compared to the oar shaft may require a relatively large heat transfer to produce a measurement. Needing a large heat transfer may result in a significant time lag time between an actual temperature change in the structure of the oar and its detection by the temperature sensor.

Preferably, using a temperature sensor with a relatively small thermal mass, such as a thin-film temperature sensor with dimensions of approximately 0.2×0.5×0.003 inches, a small thermistor, such as the PS103J2 manufactured by US Sensor Corp. of Orange, Calif., having a diameter of approximately 0.05 of an inch, a small metal-resistance temperature detector (RTD), a small thermocouple, or a small integrated-circuit temperature sensor reduces or eliminates a lag time between an actual temperature change in the structure of the oar and detection of such temperature change. In preferred constructions, temperature sensors have dimensions that are approximately equal to or less than the thickness of the wall of the oar shaft, which is commonly 0.05 to 0.06 of an inch.

Preferably, such temperature sensors produce temperature signals that closely change with the actual oar temperature changes. Preferable considerations for selecting a temperature sensor include whether the temperature sensor is suitable for the attachment method (embedding in a material, adhering to a surface, etc.), whether the temperature sensor is stable in response to thermal cycling and aging, and whether a detectable temperature signal can be obtained with a relatively low operating power. Sensor kit components may be mounted on a common board, or may be independently embedded or otherwise suitably located in oar 10.

Embedding a temperature sensor 44 into an oar shaft having a composite construction is likely to be facilitated by using a temperature sensor of small dimensions. Preferably, a temperature sensor, such as thin-film temperature sensor 44, is placed within a thermal environment that affects a deflection sensor, such as strain gage 42. In other words, a temperature sensor is preferably located as closely as possible to a deflection sensor so the temperature sensor generates a temperature signal indicative of the temperature of the material in or on which the deflection sensor is located.

The sensor kit 40 is designed to measure the magnitude of a force applied to oar 10 using a strain gage 42 (FIG. 2) and a thin-film temperature sensor 44 (FIG. 3), discussed below. Alternatively, sensor kit 40 may use an acoustic resonance frequency sensor or fiber optics to measure deflection. Preferable considerations for selecting a deflection sensor include the number of axes the sensor has (with one being preferable), whether the sensor is designed for relatively low power consumption (for example, by having a relatively high resistance), and whether the sensor is suitable for the intended attachment method (such as embedding or adhesively attaching to a surface). In the preferred embodiment described, sensor kit 40 is embedded within hollow oar shaft 16, for example, in the material that composes oar shaft 16 or in the hollow interior of oar shaft 16. Sensor kit 40 is preferably located under collar 24 which forms an additional protective covering over sensor kit 40. Alternatively, sensor kit 40 may be affixed to the outside surface of oar shaft 16, for example, by bonding to the outside surface with a weather resistant epoxy compound, and is preferably located under an overlying material such as collar 24 for protection from the elements, to reduce the rate of temperature change that would otherwise be experienced by an exposed temperature sensor, or both. Other suitable overlying materials, such as a closed-cell foam overlay, or a small rigid shell, may be used for protection, to reduce the rate of temperature change, or both.

Inner and outer grips 20 and 22 define a region of handle 18 that, in the preferred embodiment described, contains display 50. The display 50 is preferably an eight character organic light emitting diode display, or alternatively, a light emitting diode display, graphic liquid crystal display, or other suitable display. The display 50 is preferably visible to a rower while rowing and provides immediate feedback to the rower regarding rowing performance. A bright color screen 52 preferably allows information to be easily read at a high stroke rate. The display 50 has a height that is roughly the same length as the diameter of handle 18 on a standard crew oar 10. The display 50 has a width that is sized to fit between inner and outer grips 20 and 22 along the length of oar 10. The display 50 has a depth that is shallow enough to be substantially flush mounted and implanted within handle 18 along the length of oar 10. Alternatively, the display 50 may be detachably strapped around handle 18 between inner and outer grips 20 and 22.

Figure 2:
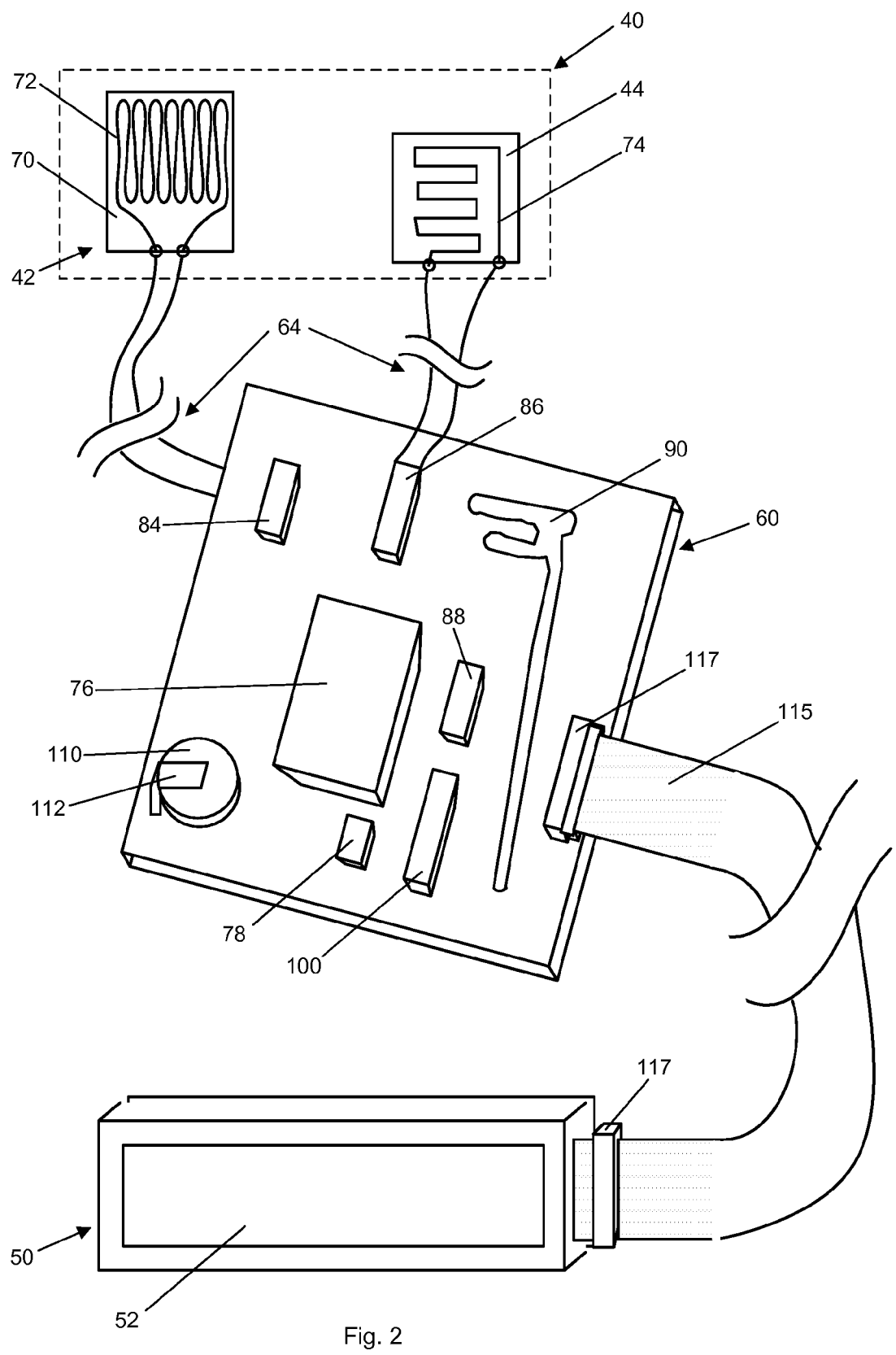
FIG. 2 is an isometric view of a sensor kit, circuit board, and display device of the oar of FIG. 1.

Circuit board 60 is also located in a region of handle 18 between inner and outer grips 20 and 22. In a preferred embodiment, the circuit board 60 is mounted in the void space of oar shaft 16 directly behind and electrically connected to the display 50 with a short ribbon cable 115 (FIG. 2). Locating the circuit board 60 in the handle 18 preferably protects the circuit board so daily handling of oar 10 is not likely to damage the circuit board 60. Additionally, locating circuit board 60 in handle 18 preferably provides for relatively short electrical connections between the display 50 and the circuit board 60, which in turn preferably results in more efficient manufacturing or replacement procedures. The circuit board 60 is electrically connected to power source 30 via electrical wire 62. Electrical power is conveyed from circuit board 60 to display 50 through an electrical connection. The circuit board 60 is electrically connected to sensor kit 40 with signal wires 64 to receive deflection and temperature signals for processing. In an alternative embodiment, the circuit board 60 may be wirelessly connected to the sensor kit 40.

FIG. 2 shows in greater detail the components of sensor kit 40, display 50, and circuit board 60. With respect to FIG. 2, an exemplary sensor kit 40 contains strain gage 42 that includes an insulating flexible backing 70 which supports a metallic foil pattern 72. As oar 10 is deformed, foil 72 is deformed, causing strain gage 42 electrical resistance to change accordingly. This resistance change, preferably measured using a Wheatstone bridge, results in a deflection signal that is proportional to the strain or force acting on oar 10.

In addition to mechanical forces attributable to a rower, strain gage 42 is also responsive to changes in the temperature of the portion. Because of changes in ambient temperature, the oar 10 changes in length due to thermal expansion and contraction of oar shaft 16. The changes in length produce strain that is detected by strain gage 42. Temperature changes also affect the stiffness of oar 10, which has the effect of allowing more or less bend in oar shaft 16 under a load. Such temperature dependent effects interfere with the analysis of deflection signals that are caused from mechanical forces attributed to a rower. To calibrate for such temperature effects, temperature sensor 44 is co-located with strain gage 42 to provide a temperature signal representative of the temperature around the area of oar shaft 16 containing the strain gage 42. Such temperature signals preferably permit temperature effects on the deflection signal to be considered when analyzing the strain signal, for example, through signal processing, to produce actual force magnitude data based on the force applied by a rower. Such temperature compensation also preferably permits calculation of derived rowing data magnitude with respect to distance or time.

In a preferred embodiment, the temperature sensor 44 is a thin-film resistance temperature device having a metal wire 74. The electrical resistance of the metal wire 74 changes as its temperature changes. Although the electrical resistance of the temperature sensor 44 changes with temperature fairly linearly, software processing can curve fit non-linear effects to increase the accuracy of temperature sensor 44 at higher temperature differentials.

The sensor kit 40 conveys the deflection and temperature signals by electrical wire connection to a processor 76 that receives a clock signal from a crystal oscillator 78 and manipulates data stored in one or more of random access memory, flash memory, or other suitable memory. The deflection signal is preferably digitized in a standalone analog-to-digital converter microchip 84, or alternatively by an analog-to-digital converter integrated into the processor 76. The temperature signal is preferably digitized in a standalone analog-to-digital converter microchip 86, or alternatively by an analog-to-digital converter integrated into the processor 76.

Figure 3:
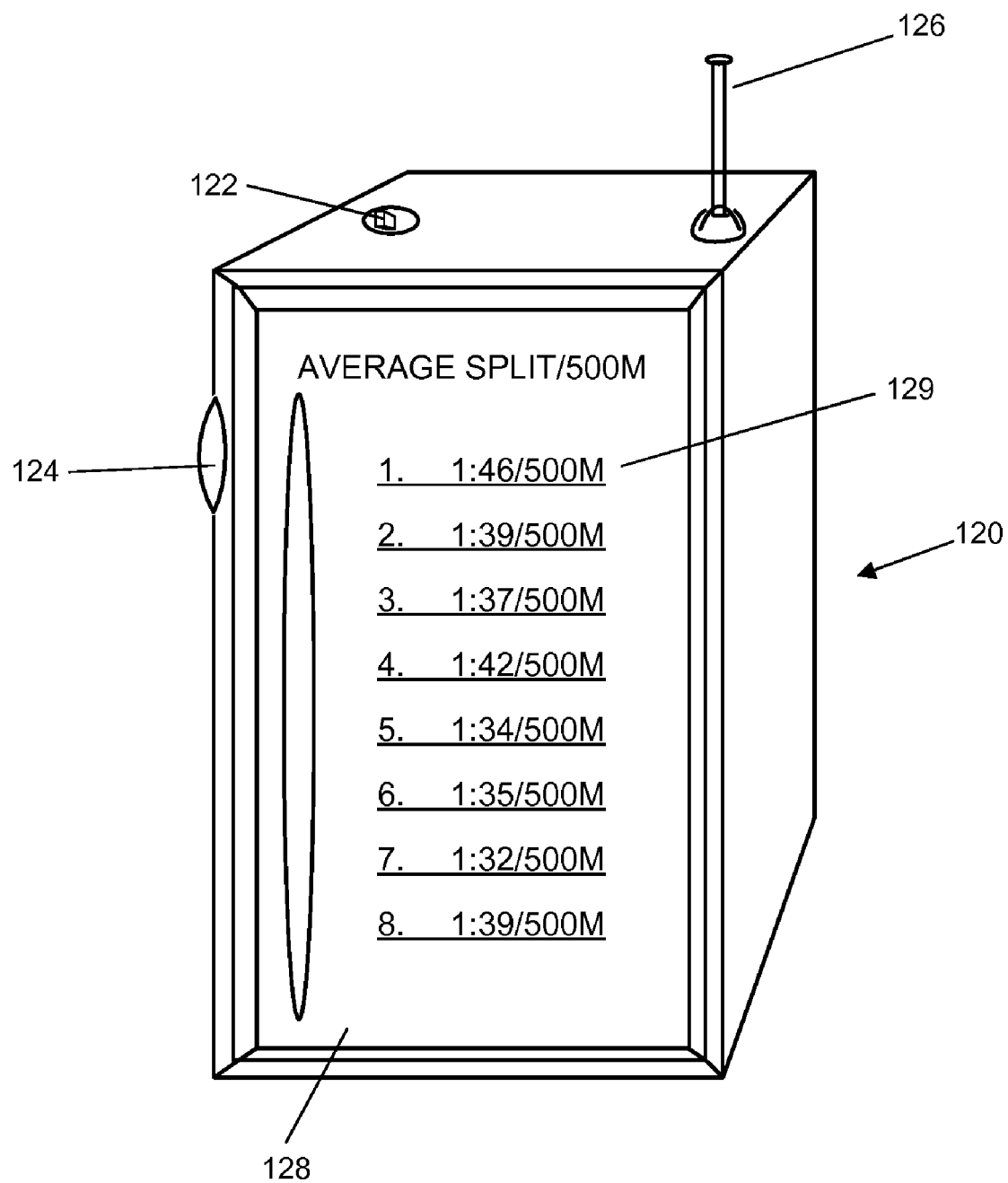
FIG. 3 is an isometric view of a remote display device for use with the oar of FIG. 1.

In a preferred embodiment, force magnitude data and derived rowing data is transmitted wirelessly to a remote display device (FIG. 3). The processor 76 is preferably a microcontroller electrically connected to a wireless transceiver 88. An antenna 90 formed on printed circuit board 60 is electrically connected to wireless transceiver 88 and provides a low cost internal antenna for antenna signals. An amplifier 100 increases the magnitude of any one of the signals produced by deflection sensor 42, temperature sensor 44, or antenna 90 when the signal is too small to be detected by processor 76 input ports. The signals are amplified and then conveyed to the processor 76 input ports. The circuit board 60 is powered by power source 30. An alternative embodiment shown in FIG. 2 is a battery 110 that is seated in a retaining clip 112 that is electrically connected to circuit board 60. In this embodiment, the battery 110 is replaceable by removing circuit board 60 from handle 18.

The display 50 is electrically connected to circuit board 60 through a ribbon cable 115 and associated ribbon cable snap connectors 117, at the circuit board 60 and display 50, respectively. Alternatively, the display 50 is directly electrically connected to circuit board 60 through a set of electrical pins on circuit board 60 that interengage a female connector on display 50. The display 50 receives instructions from processor 76 to scroll through derived rowing data on screen 52. Derived rowing data may include a time-series of measurement data that is recorded during a single application of force to the oar 10. For example, the derived rowing data may include a cumulative total of magnitudes of the force acting on the oar blade during a selected time period, which may be expressed by the following equation:

$$\text{Impulse} = \int_{t_1}^{t_2} F \, dt \qquad \text{Equation (1)}$$

where F is the force applied during the selected time period $t_1$ to $t_2$. Some embodiments may include an average of the magnitude of the force acting on the oar blade during the selected time period; a cumulative total of the magnitude of the force acting on the oar blade during a distance rowed; an average of magnitude of the force acting on the oar blade during the distance rowed; or a number of rowing strokes per a unit of time, the number of rowing strokes calculated from a periodic change in the magnitude of the force acting on the oar blade. In another example, a force application profile may contain information that includes peak and average values of force applied to oar 10 during a stroke as well as when the largest amount of force was applied during the stroke. Other derived rowing data may include time and stroke dependent information such as a rower's average split time for a known distance, a rower's stroke rate over a known time, duration of a rower's workout, or other suitable information based on number of rowing strokes, time for an individual stroke, time for a series of strokes, force applied to individual strokes, force applied to a number of rowing strokes, or other suitable force or time data.

Alternatively, the display device 50 may be remotely located from the oar. In one embodiment, the coach uses the force information or derived rowing data on a handheld device capable of being used remote from a rowed boat to indicate how hard each rower is pulling during each rowing piece. The coach may also use the handheld device to synchronize the rowing data among a set of oars, thereby allowing the coach to make sure the strongest rowers are in a boat to make the fastest boat possible. For example, a coach could command each oar 10 to erase its memory of a previous workout, to concurrently start sending signals for a workout, or other suitable synchronization command.

FIG. 3 shows a preferred embodiment of a remote display device 120 that includes an on/off button 122 that turns the remote display device 120 on or off. Remote display device 120 also includes a start/stop button 124 that starts or stops recording wirelessly received data transmitted from the oar 10 wireless transceiver 88. The antenna 126 provides a strong antenna signal connection when the remote display device 120 is far from the wireless transceiver 88. Display screen 128 of remote display device 120 is preferably a touch screen that allows a coach to manipulate and look more closely at a specific rower's data obtained from oar 10.

In a preferred embodiment, a coach sets up a rowing practice that includes individual rowing workout (rowing pieces) on the water. The coach then selects on remote display device 120 the specific practice pieces for the rowers to do. The coach may then press start/stop button 124 to begin recording data or to end the timing for the pieces. As the rower takes a stroke through the water associated processing for deflection sensor 42 and temperature sensor 44 determines the amount of force the rower exerted against the water. This force data is then converted into an easily understandable split that mimics a readout of a split on an ergometer. The rower may then read this information on display 50 and the information is also transmitted to the remote display device 120. The coach receives the transmission from oar 10 wirelessly and can see the outline of the selected 8+, 4+, or pair rowing shell, on a line 129 designating each seat of the selected shell with a display of an average split for each rower in each seat of the selected shell that is using an oar 10.

Figure 4:
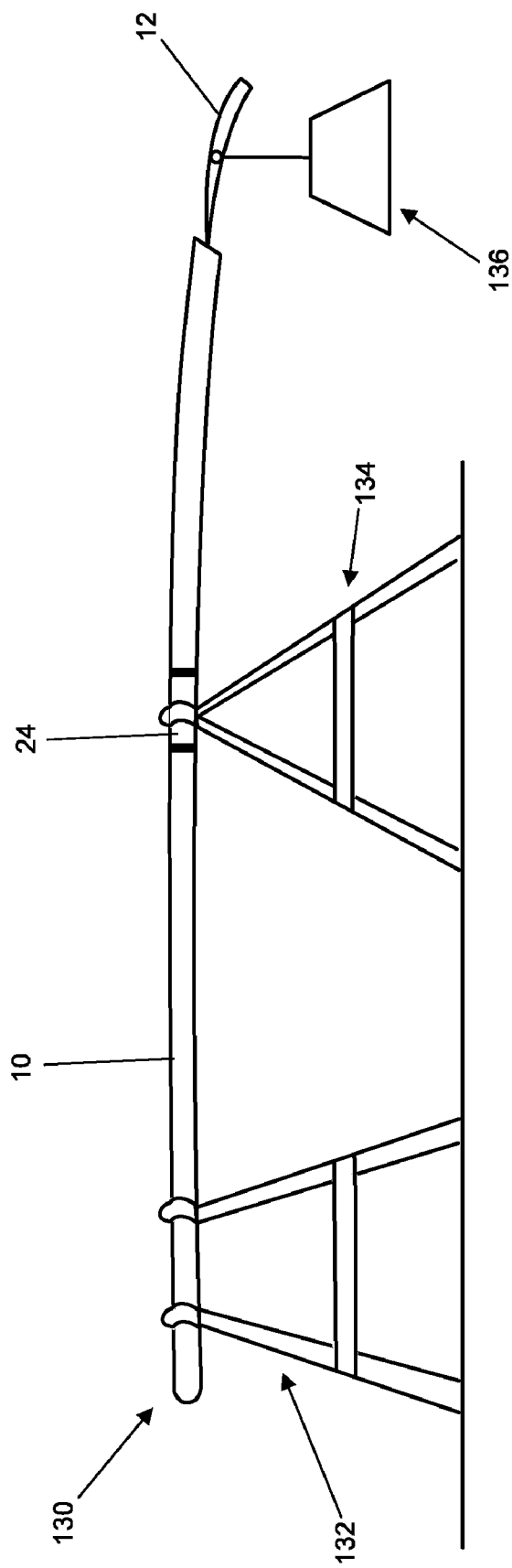
FIG. 4 is an elevation view of a calibration device for an oar according to a preferred embodiment.

FIG. 4 shows a calibration device 130 for calibrating oar 10. A preferred calibration method includes placing the oar 10 in a handle-grip stand 132, placing the collar 24 in a simulated oar lock stand 134, and hanging a calibration weight 136 in a prescribed position on the oar shaft 16 or oar blade 12. Software executing on processor 76 operating in a calibration mode stores measurements of deflection and temperature signals resulting from the presence of different calibration weights 136 at different temperatures. Such software preferably determines the relationship between the signals at a known oar load in pounds or kilograms and associates such signals with the known oar load. Such calibration can be performed by persons of limited skill. Easy repetition of the calibration process preferably provides confidence in the measurement of force during rowing.

Another advantage of calibration device 130 is that calibration can readily be conducted throughout the life of oar 10. It is possible that aging and exposure to ultraviolet radiation could alter the stiffness of oar shaft 16 to an extent that could result in the signals associated with known forces no longer being associated with a known force. For example, if the material of oar shaft 16 becomes stiffer over time a known force will bend the oar shaft 16 to a lesser degree. Thus, signals associated with a known force, which correlates to a known amount of bending, would no longer accurately be associated with a correct force amount. Periodic use of calibration device 130 preferably provides a record of how much force is required to bend the oar shaft 16, even as the material properties of the oar shaft 16 change over time.

It will be obvious to those having skill in the art that many changes may be made to the details of the above-described embodiments without departing from the underlying principles of the invention. The scope of the present invention should, therefore, be determined only by the following claims.

The invention claimed is:

1. A system for determining a force on an oar during a rower's rowing stroke in water, comprising:

an oar handle;

an oar shaft extending from the oar handle;

an oar blade affixed to the oar shaft distal from the oar handle;

a deflection sensor affixed to a portion of the oar shaft for sensing oar shaft deflection, wherein the deflection sensor generates a deflection signal in response to deflection of the oar shaft resulting from a force acting on the oar blade;

a temperature sensor affixed to a portion of the oar shaft proximate the deflection sensor to generate a temperature signal representing a temperature of the portion of the oar shaft;

a processing device mounted to the oar, the processing device operatively coupled to the deflection sensor and the temperature sensor to receive the deflection signal and the temperature signal, the processing device programmed to determine a magnitude of the force acting on the oar blade based on the received deflection signal and temperature signal and to generate data representing the magnitude of force;

a display device in communication with the processing device to receive from the processing device the data representing the magnitude of force; and a power source electrically connected to and provides power to the deflection sensor, the temperature sensor, and the processing device.

2. The system of claim 1, wherein the processing device is further programmed to determine the magnitude of the force acting on the oar blade based on a table lookup function.

3. The system of claim 1, wherein the temperature sensor includes a thin-film temperature sensor and the deflection sensor includes a strain gage.

4. The system of claim 1, wherein:

the oar shaft includes a generally tubular wall; and the deflection sensor and the temperature sensor are embedded in the tubular wall of the oar shaft.

5. The system of claim 1, wherein the deflection sensor and the temperature sensor are affixed on an inside surface of the oar shaft.

6. The system of claim 1, wherein the deflection sensor and the temperature sensor are affixed to an outside surface of the oar shaft.

7. The system of claim 6, further comprising an oar collar secured to the oar shaft over the deflection sensor.

8. The system of claim 1, wherein the processing device is communicatively coupled with the deflection sensor and the temperature sensor via a signal wire.

9. The system of claim 1, wherein the processing device is further programmed to determine derived rowing data based on the determined force magnitude, wherein the derived rowing data includes one or more of:

a cumulative total of the magnitude of the force acting on the oar blade during a selected time period;

an average of the magnitude of the force acting on the oar blade during the selected time period;

a cumulative total of the magnitude of the force acting on the oar blade during a distance rowed;

an average of the magnitude of the force acting on the oar blade during the distance rowed; and a number of rowing strokes per a unit of time, the number of rowing strokes calculated from a periodic change in the magnitude of the force acting on the oar blade.

10. The system of claim 9, further comprising a memory storage device communicatively coupled to the processing device for storing the derived rowing data.

11. The system of claim 9, wherein the display device is located remotely from the oar, further comprising:

a wireless transceiver mounted to the oar and operatively connected to the processing device for transmitting the derived rowing data to the remote display device; and wherein the power source is further electrically connected to and provides power to the wireless transceiver.

12. The system of claim 11, wherein:

the remote display device is configured to receive and differentiate derived rowing data from a plurality of oars; and the remote display device includes an interface for displaying the derived rowing data from each oar sequentially or simultaneously.

13. The system of claim 12, wherein the remote display device is communicatively coupled to the plurality of oars, the remote display device is configured to transmit commands to the plurality of oars for synchronizing the derived rowing data.

14. The system of claim 11, further comprising a memory storage device operatively coupled to the remote display device for storing the derived rowing data.

15. The system of claim 9, wherein the display device includes an electronic display attached to a surface of the oar and visible to a rower while rowing, the electronic display configured to display the derived rowing data; and the power source is further electrically connected to and provides power to the display device.

16. A method of determining derived rowing data for a rower's rowing stroke in water, comprising:

generating with a deflection measuring device, a deflection signal in response to deflection of an oar shaft of an oar;

generating with a temperature measuring device proximate the deflection measuring device, a temperature signal based on a temperature of the oar shaft;

determining a force on the oar based on the deflection signal and the temperature signal;

generating with a processor, derived rowing data based on the determined force, wherein the derived rowing data includes one or more of:

a cumulative total of the magnitude of the force acting on the oar blade during a selected time period;

an average of the magnitude of the force acting on the oar blade during the selected time period;

a cumulative total of the magnitude of the force acting on the oar blade during a distance rowed;

an average of the magnitude of the force acting on the oar blade during the distance rowed; and a number of rowing strokes per a unit of time, the number of rowing strokes calculated from a periodic change in the magnitude of the force acting on the oar blade; and displaying the derived rowing data on a display.

17. The method of claim 16, wherein displaying the derived rowing data includes displaying the derived rowing data to the rower.

18. The method of claim 16, wherein the display is remotely located from the oar, the method further comprising:

transmitting the derived rowing data to the display.

* * * * *